US00PP08967P

United States Patent [19]

Klemm

[11] Patent Number: Plant 8,967

[45] Date of Patent: Nov. 1, 1994

[54] GERANIUM NAMED KLEGARBO

[75] Inventor: Siegfried Klemm, Stuttgart, Germany

[73] Assignee: Klemm & Sohn, Stuttgart-Muhlhausen, Germany

[21] Appl. No.: 173,671

[22] Filed: Dec. 23, 1993

[51] Int. Cl.[5] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Tilton, Fallon, Lungmus & Chestnut

[57] ABSTRACT

A new geranium cultivar particularly distinguished by its round shape and compact growth, early appearing pink flowers in an upright cluster over medium-green foliage with good precocity and floral richness.

1 Drawing Sheet

BACKGROUND OF THE NEW PLANT

The present invention comprises a new and distinct cultivar of geranium, botanically known as *Pelargonium zonale*-Hybride. The new cultivar is propagated from cuttings resulting from the cross of Diva and D-316. Diva is a pink colored geranium having semi-double flowers which grows very compact. Diva is not commercially available and is not known by any synonyms. D-316 is a light violet colored geranium also having semi-double flowers and does not grow very compact. D-316 is not commercially available and is not known by any synonyms. Neither Diva or D-316 has been patented. As a result of this cross the present cultivar was created in 1989 in Stutgart, Germany and has been repeatedly asexually reproduced by cuttings in Stuttgart, Germany and Teneriffe, Italy over a four year period. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to The R.H.S. Color Chart of The Royal Horticultural Society of London.

THE PLANT

Classification:
- *Botanical.*—*Pelargonium zonale*-Hybride.
- *Commercial.*—Zonal geranium.

Parentage:
- *Seed parent.*—Collected seed from Diva, a seedling our D-generation of plants bred in 1985.

- *Pollen parent.*—A seedling named D-316 is one of our seedlings from our D-generation of plants bred in 1985.

Form: Very compact bush.
Shape: Round.
Height: About 190–210 mm in April and 230–240 mm in September.
Stem length: 80–115 mm depending on the season.
Number of stems per stalk: Approximately 8–9 from May until the end of September.
Number of stalks per plant: Approximately 12–13 in October.
Internode length: About 6–15 mm depending on the light where the plant is propagated.
Growth rate: Upright and vigorous.
Strength: Very good.
Branching character: Very good branching.
Foliage:
- *Quantity.*—Many robust leaves.
- *Size.*—Small — From 55×55 mm to 70×60 mm.
- *Shape.*—Round.
- *Margin.*—Bicrenate.
- *Texture.*—Smooth.
- *Zonation.*—Very weak zonation.

Ribs and veins: None.
Color:
- *Upper side.*—Medium green RHS 137-A.
- *Under side.*—Light green — RHS 147-B.

Length of leaf stem: About 40–45 mm.

THE BUD

Size: Medium.
- *Diameter.*—About 8 mm.
- *Length.*—About 9 mm.
- *Depth.*—About 12 mm.

Shape: Elliptical.
Form: Ovoid and pointed.
Rate of opening: Medium.
Color:
- *When sepals first divide.*—Very light pink, almost white RHS 62-D.
- *When the petals begin to unfurl.*—The inside of the petal is seen. The inside of the petal is much darker than the border of the petal which is RHS 57 C/D in color.

Sepals:
- Numbers.—5.
- *Shape.*—Long and Pointed.

*Color.*—Inside — Light green RHS 147-B. Outside — Light green RHS 147-B.

*Form.*—Standing up.

Petiole of floret:

*Length.*—About 22 mm.

*Strength.*—Very strong. The florets are arranged hemispherically around the middle of the cluster. The florets are 42–44 mm in diameter.

*Color.*—Green — RHS 146-C.

THE FLOWER

Blooming habit: Continuous and profusely from April until October.

Size: Approximately 42–44 mm.

Borne: In a cluster having between about 60–70 florets per cluster.

Form: Cup.

Changes of the form with maturity: The bloom becomes a little flat.

Petals:

*Numbers.*—About 6–7 per floret. Between 280–300 clusters in one season on three plants (from May until the end of September). There are approximately 75–100 clusters per plant in one season.

*Arrangement.*—Imbricated.

*Form.*—Entire broad.

*Color.*—Outer petal: The body is RHS 68-B in color. The base is RHS 68-B in color. Inside petal: The body is 68-B in color. The base is 68-C in color. Reverse side: RHS 65-D in color.

*Pattern.*—At least two of the top mature petals of each floret variably express a pattern which includes a red, blush-like spot in the central portion of the petal which effuses or bleeds, progressively into the predominant light purple color of the top surface of the margin. The spots are separated from the attachment points of these petals by a generally white, basal zone of substantially white color, except for the veins, which have the same color as the spot and from striations communicating the spot to the petal attachment points. These markings may be wholly or partly obscured by the overlying petaloids do not express similar color markings. The pattern described above is close to the center of the floret and is partly mashed by the petaloids.

*Texture.*—Soft.

*Appearance.*—Satiny.

How long do petals remain on stem: About five-seven days depending on the weather.

Petaloids:

*Number.*—About 2 to 3.

*Size.*—Approximately 3–4 mm.

*Color.*—Light pink.

Persistence: Matured florets or clusters should be picked off.

Disease resistance: Klegarbo does not suffer from Botrytis.

Weather resistance: Klegarbo is not unusually affected by wet or hot weather.

Lasting quality:

*On the living plant in pot.*—About 18–21 days.

*As a cut flower.*—About 6 days.

Fragrance: No perceptible fragrance.

REPRODUCTIVE ORGANS

Stamens:

*Anthers.*—Seven positioned around the ovaries about 2.5 mm length.

*Filaments.*—About 5.5 mm in length and white in color.

Pollen: Orange in color.

Pistils:

*Number.*—One.

*Length.*—Approximately 7 mm.

*Stigmas.*—Pink in color.

Ovaries: Green in color.

Seed: Fertile.

*Shape.*—Ovoid.

*Color at maturity.*—Dark brown.

I claim:

1. A new and distinct geranium cultivar substantially as herein shown and described, particularly distinguished by its very round shape and compact growth and its early appearing pink flowers in an upright cluster over medium green foliage.

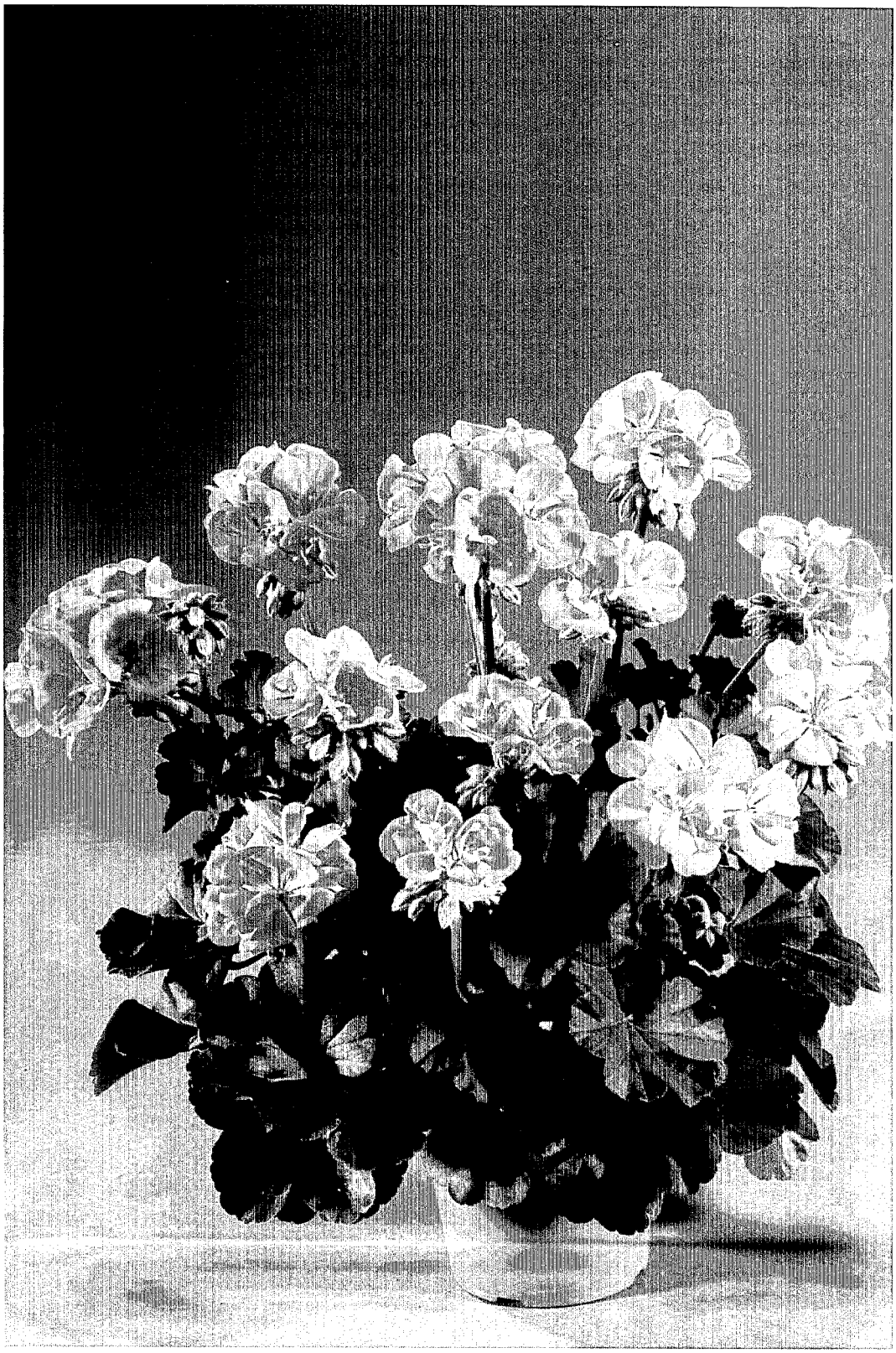

* * * * *